(12) United States Patent
Sharareh et al.

(10) Patent No.: US 7,662,152 B2
(45) Date of Patent: Feb. 16, 2010

(54) CATHETER WITH MULTI PORT TIP FOR OPTICAL LESION EVALUATION

(75) Inventors: Shiva Sharareh, Laguna Niguel, CA (US); Ariel Garcia, Duarte, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 647 days.

(21) Appl. No.: 11/453,188

(22) Filed: Jun. 13, 2006

(65) Prior Publication Data

US 2007/0287998 A1    Dec. 13, 2007

(51) Int. Cl.
 *A61B 18/18* (2006.01)
(52) U.S. Cl. .......................................... 606/41; 606/15
(58) Field of Classification Search ................. 606/1–41
 See application file for complete search history.

(56) References Cited

U.S. PATENT DOCUMENTS

| 4,587,972 | A |   | 5/1986  | Morantte, Jr. |
|-----------|---|---|---------|---------------|
| 5,041,109 | A | * | 8/1991  | Abela ........................... 606/15 |
| 5,248,311 | A | * | 9/1993  | Black et al. .................... 606/15 |
| 5,391,199 | A |   | 2/1995  | Ben-Haim |
| 5,443,489 | A |   | 8/1995  | Ben-Haim |
| 5,480,422 | A |   | 1/1996  | Ben-Haim |
| 5,546,951 | A |   | 8/1996  | Ben-Haim |
| 5,558,091 | A |   | 9/1996  | Acker et al. |
| 5,568,809 | A |   | 10/1996 | Ben-haim |
| 5,693,043 | A | * | 12/1997 | Kittrell et al. ................. 606/15 |
| 5,830,209 | A | * | 11/1998 | Savage et al. ................. 606/15 |
| 5,964,757 | A |   | 10/1999 | Ponzi |
| 6,602,242 | B1|   | 8/2003  | Fung et al. |

FOREIGN PATENT DOCUMENTS

| EP | 0 195 375 A | 9/1986 |
| EP | 0 441 040 A | 8/1991 |
| WO | WO 95/02995 | 2/1995 |

OTHER PUBLICATIONS

International Search Report and Written Opinion of the International Searching Authority, International Application No. PCT/US2007/071107, mailed Nov. 19, 2007.

* cited by examiner

*Primary Examiner*—Linda C Dvorak
*Assistant Examiner*—Amanda Scott
(74) *Attorney, Agent, or Firm*—Christie, Parker & Hale, LLP.

(57) ABSTRACT

A catheter is adapted to ablate tissue and provide optically-based lesion qualitative and quantitative monitoring, comprising a catheter body and a tip electrode distal the catheter body adapted for ablating tissue, the tip electrode having a shell and an alignment member defining a hollow distal portion therebetween. In accordance with the invention, the catheter further includes a plurality of optical waveguides adapted to transmit optical energy to and from the tip electrode. A distal portion of each waveguide extends through the hollow distal portion and terminates in openings formed in the shell. Advantageously, the alignment member fixedly secures the distal portion of each waveguide against movement relative to the alignment member and the shell.

17 Claims, 14 Drawing Sheets

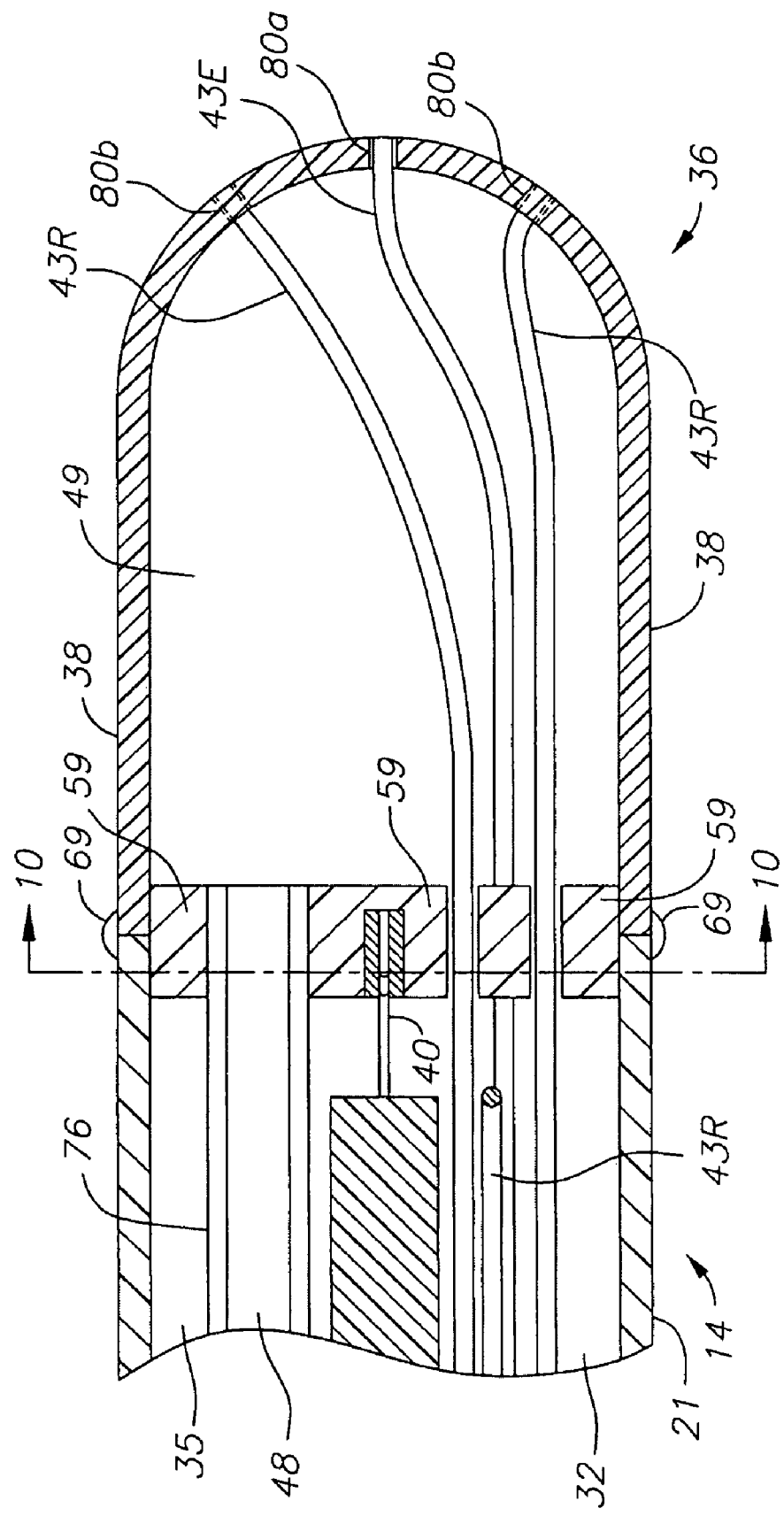

CATHETER WITH MULTI PORT TIP FOR OPTICAL LESION EVALUATION

FIELD OF INVENTION

The present invention relates to ablation catheters, and in particular to ablation catheters with lesion monitoring.

BACKGROUND

For certain types of minimally invasive medical procedures, real time information regarding the condition of the treatment site within the body is unavailable. This lack of information inhibits the clinician when employing catheter(s) to perform a procedure. An example of such procedures is tumor and disease treatment in the liver and prostate. Yet another example of such a procedure is surgical ablation used to treat atrial fibrillation. This condition in the heart causes abnormal electrical signals, known as cardiac arrhythmias, to be generated in the endocardial tissue resulting in irregular beating of the heart.

The most frequent cause of cardiac arrhythmias is an abnormal routing of electricity through the cardiac tissue. In general, most arrhythmias are treated by ablating suspected centers of this electrical misfiring, thereby causing these centers to become inactive. Successful treatment, then, depends on the location of the ablation within the heart as well as the lesion itself. For example, when treating atrial fibrillation, an ablation catheter is maneuvered into the right or left atrium where it is used to create ablation lesions in the heart. These lesions are intended to stop the irregular beating of the heart by creating non-conductive barriers between regions of the atria that halt passage through the heart of the abnormal electrical activity.

The lesion should be created such that electrical conductivity is halted in the localized region (transmurality), but care should be taken to prevent ablating adjacent tissues. Furthermore, the ablation process can also cause undesirable charring of the tissue and localized coagulation, and can evaporate water in the blood and tissue leading to steam pops.

Currently, lesions are evaluated following the ablation procedure, by positioning a mapping catheter in the heart where it is used to measure the electrical activity within the atria. This permits the physician to evaluate the newly formed lesions and determine whether they will function to halt conductivity. It if is determined that the lesions were not adequately formed, then additional lesions can be created to further form a line of block against passage of abnormal currents. Clearly, post ablation evaluation is undesirable since correction requires additional medical procedures. Thus, it would be more desirable to evaluate the lesion as it is being formed in the tissue.

A known method for evaluating lesions as they are formed is to measure electrical impedance. Biochemical differences between ablated and normal tissue can result in changes in electrical impedance between the tissue types. Although impedance is routinely monitored during electrophysiologic therapy, it is not directly related to lesion formation. Measuring impedance merely provides data as to the location of the tissue lesion but does not give qualitative data to evaluate the effectiveness of the lesion.

Another approach is to measure the electrical conductance between two points of tissue. This process, known as lesion pacing, can also determine the effectiveness of lesion therapy. This technique, however, measures only the success or lack thereof from each lesion, and yields no real-time information about the lesion formation.

Thus, there is a need for a catheter capable of measuring lesion formation, as well as detecting the formation of charred tissue and coagulated blood around the ablation catheter. Where such measuring and detection use fiber optics, there is a further need for a catheter that provides sufficient room in the tip to accommodate multiple fiber optics for multi-directional emission and collection of light, as well as other components such as a navigational sensors, temperature sensor and/or deflection elements. It is also desirable that such a catheter provide irrigation for cooling the tip electrode and/or creating deeper and larger lesions.

SUMMARY OF THE INVENTION

The present invention is directed to a catheter that is adapted for ablation and provides optically-based lesion qualitative and quantitative information. The catheter comprises a catheter body and a tip electrode distal the catheter body adapted for ablating tissue where the tip electrode has a shell and an alignment member defining a hollow distal portion therebetween. In accordance with the invention, the catheter further includes a plurality of optical waveguides adapted to transmit optical energy to and from the tip electrode. Lesion assessments are accomplished by measuring the light intensity at one or more wavelengths that is recaptured at the catheter tip resulting from the light radiated from the catheter tip onto ablated tissue. A distal portion of each waveguide extends through the hollow distal portion and terminates in openings formed in the shell. Advantageously, the alignment member fixedly secures the distal portion of each waveguide against movement relative to the alignment member and the shell to minimize stress and strain on waveguides that may cause breakage.

In a detailed embodiment, the distal portion of each waveguide has a fixed flexure configuration within the hollow distal portion of the tip electrode to provide multi-directional radiation and/or collection of light at the tip electrode. Moreover, the openings in the shell of the tip electrode may include a center opening aligned with a longitudinal axis of the tip electrode and at least one off-center opening. The catheter may also be configured such that the distal portion of each waveguide is directed to transmit or receive light energy in a pattern with a radial component about the longitudinal axis. In a more detailed embodiment, the tip electrode may have three off-center openings configured equally offset from each other at about 120 degrees, to six off-center openings configured equally offset from each other at about 60 degrees.

In accordance with the invention, the light energy collected at the tip electrode conveys a tissue parameter of a lesion illuminated by light energy from the tip electrode. The tissue parameter includes at least one of the following: lesion formation, depth of penetration of lesion, cross-sectional area of lesion, formation of char during ablation, recognition of char during ablation, differentiation of char from non-charred tissue, formation of coagulum around the ablation site, differentiation of coagulated from non-coagulated blood, differentiation of ablated from healthy tissue, tissue proximity, evaluation of tissue health, status, and disease state, and recognition of steam formation in the tissue for prevention of steam pop.

The catheter may also include a temperature sensor, or an electromagnetic location sensor carried at or near the tip electrode for producing electrical signals indicative of a location of the electromagnetic location sensor. The catheter may further include means for deflecting a section of the catheter body, and/or irrigation means to provide fluid to the tip electrode and surrounding surface and tissue.

The present catheter is designed to use light. Advantageously, the light used to monitor and assess the lesion is generally not affected by the portion of the electromagnetic radiation used for ablation. Moreover, the bandwidth used for monitoring and assessing also transmits through blood with minimal attenuations. The fiber optics are used and disposed in the catheter in a manner that avoids contact with tissue, which can increase the operative lifetime of the catheter and minimize damages caused by abrasion to the fiber optics. Furthermore, the fiber optics are disposed in the tip electrode with minimal bend or strain but increased angular coverage, which can minimize fiber optics breakage during assembly and use, as well as reduce nonlinear optical effects caused by orientation of the fiber optics. In addition, the use of fiber optics to emit and receive light is a generally temperature neutral process that adds little if any measurable heat to surrounding blood or tissue.

BRIEF DESCRIPTION OF THE DRAWINGS

These and other features and advantages of the present invention will be better understood by reference to the following detailed description when considered in conjunction with the accompanying drawings wherein:

FIG. 7B is a side cross-sectional view of another embodiment of a tip electrode and a distal portion of an intermediate section, taken along a second diameter generally perpendicular to the first diameter of FIG. 7A.

DETAILED DESCRIPTION OF THE INVENTION

Figure 1:
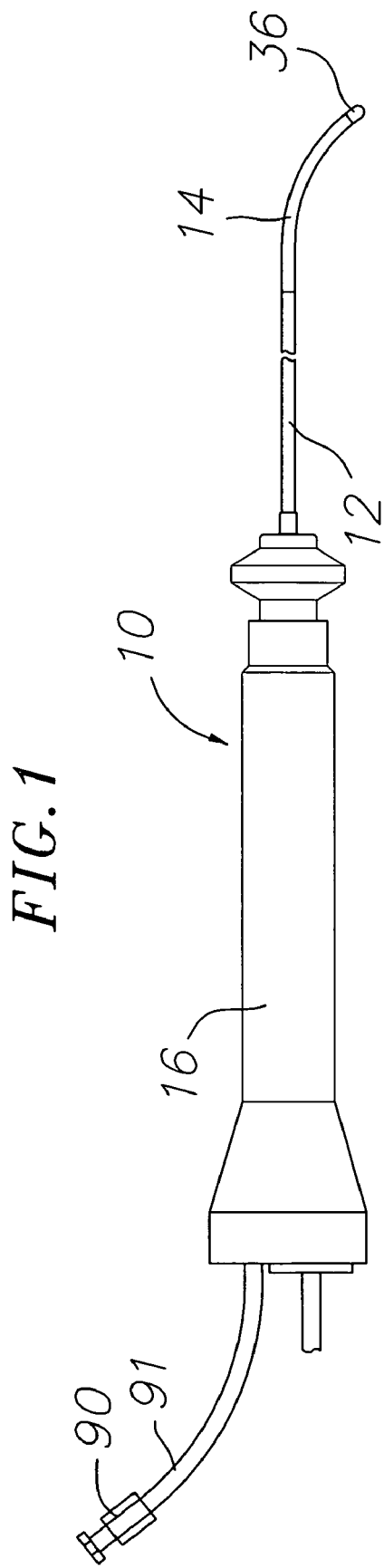
FIG. 1 is a side view of an embodiment of the catheter of the invention.

As shown in FIGS. 1-6, an embodiment of a catheter 10 in accordance with the present invention comprises an elongated catheter body 12 having proximal and distal ends, a deflectable intermediate section 14 at the distal end of the catheter body 12, a tip electrode 36 at the distal end of the intermediate section, and a control handle 16 at the proximal end of the catheter body 12.

Figure 2A:
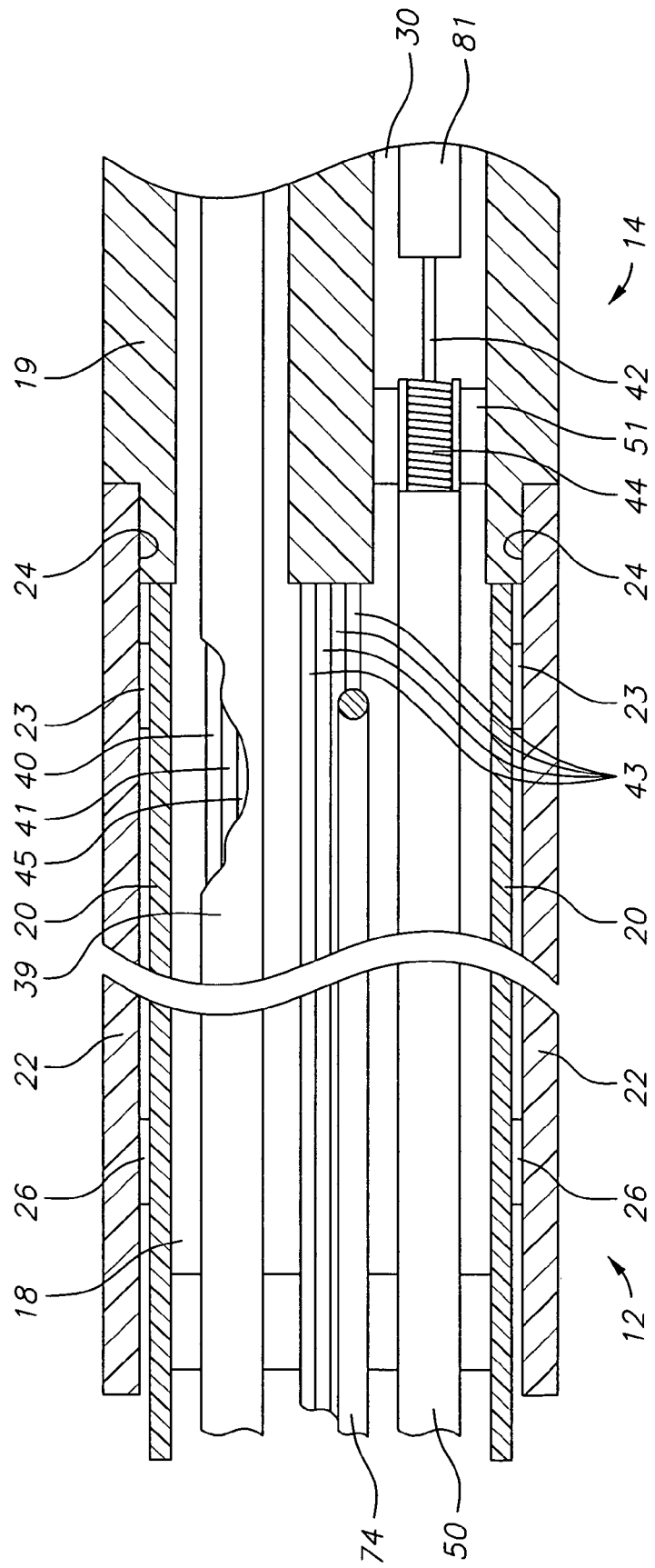
FIG. 2A is a side cross-sectional view of an embodiment of a catheter body according to the invention, including the junction between the catheter body and intermediate section, taken along a first diameter.
Figure 2B:
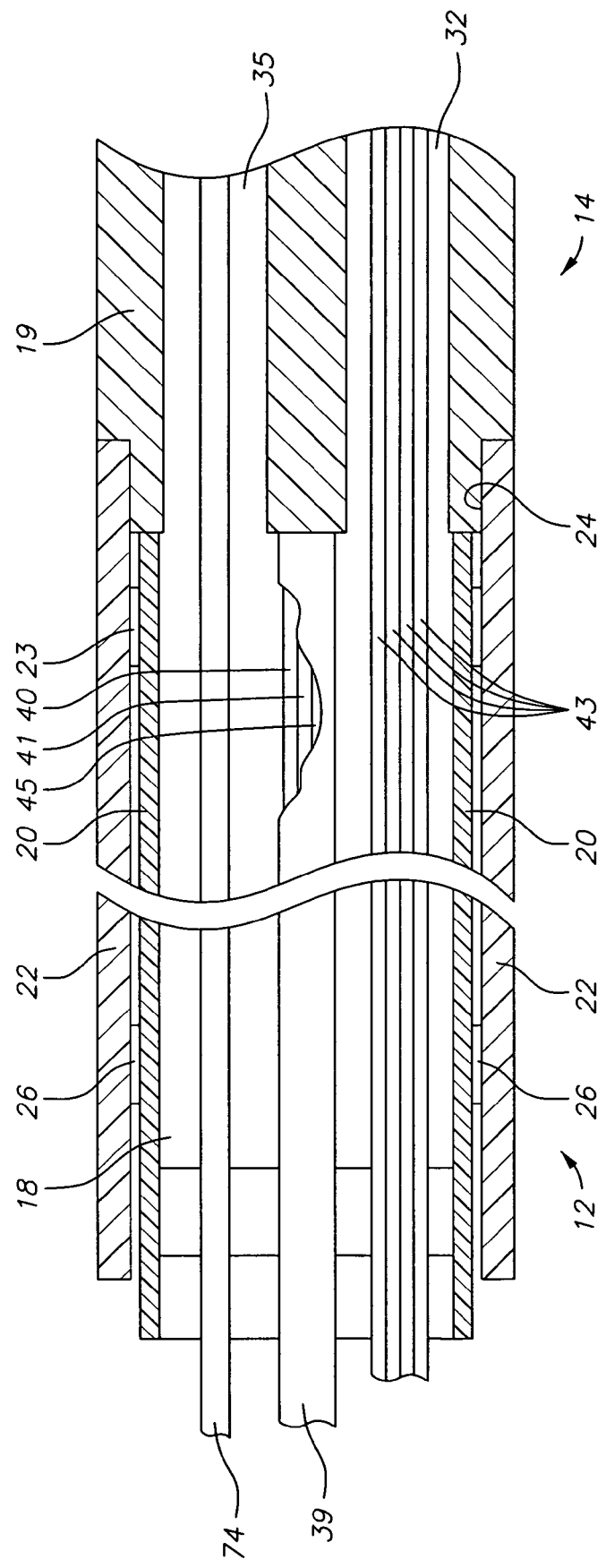
FIG. 2B is a side cross-sectional view of an embodiment of a catheter body according to the invention, including the junction between the catheter body and intermediate section, taken along a second diameter generally perpendicular to the first diameter of FIG. 2A.

With reference to FIGS. 1, 2A and 2B, the catheter body 12 comprises an elongated tubular construction having a single, axial or central lumen 18. The catheter body 12 is flexible, i.e., bendable, but substantially non-compressible along its length. The catheter body 12 can be of any suitable construction and made of any suitable material. A construction comprises an outer wall 22 made of an extruded plastic. The outer wall 22 may comprise an imbedded braided mesh of stainless steel or the like to increase torsional stiffness of the catheter body 12 so that, when the control handle 16 is rotated, the catheter body 12, the intermediate section 14 and the tip electrode 36 of the catheter 10 will rotate in a corresponding manner.

Extending through the single lumen 18 of the catheter body 12 are components, for example, a lead wire 40 and thermocouple wires 41 and 45 protected by a sheath 39, fiber optic cables 43, a compression coil 44 through which a puller wire 42 extends, and an electromagnetic sensor cable 74. A single lumen catheter body can be preferred over a multi-lumen body because it has been found that the single lumen body permits better tip control when rotating the catheter. The single lumen permits the various aforementioned components to float freely within the catheter body. If such components were restricted within multiple lumens, they tend to build up energy when the handle is rotated, resulting in the catheter body having a tendency to rotate back if, for example, the handle is released, or if bent around a curve, to flip over, either of which are undesirable performance characteristics.

The outer diameter of the catheter body 12 is not critical, but is preferably no more than about 8 french, more preferably 7 french. Likewise the thickness of the outer wall 22 is not critical, but is thin enough so that the central lumen 18 can accommodate the aforementioned components. The inner surface of the outer wall 22 may be lined with a stiffening tube 20, which can be made of any suitable material, such as polyimide or nylon. The stiffening tube 20, along with the braided outer wall 22, provides improved torsional stability while at the same time minimizing the wall thickness of the catheter, thus maximizing the diameter of the central lumen 18. The outer diameter of the stiffening tube 20 is about the same as or slightly smaller than the inner diameter of the outer wall 22. Polyimide tubing may be preferred for the stiffening tube 20 because it may be very thin walled while still providing very good stiffness. This maximizes the diameter of the central lumen 18 without sacrificing strength and stiffness.

Figure 3:
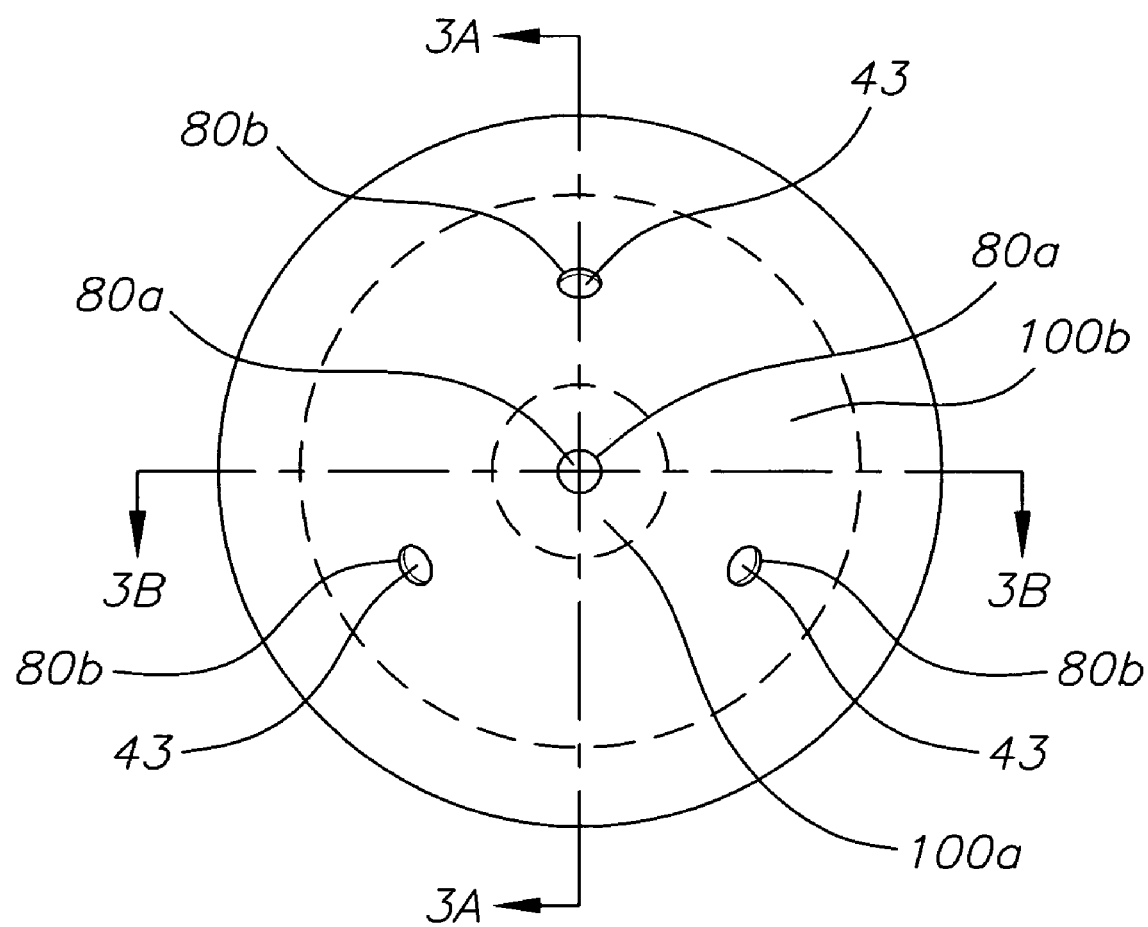
FIG. 3 is a is an end view of the distal end of an embodiment of a tip electrode showing a center opening and a plurality of off-center openings.
Figure 3A:
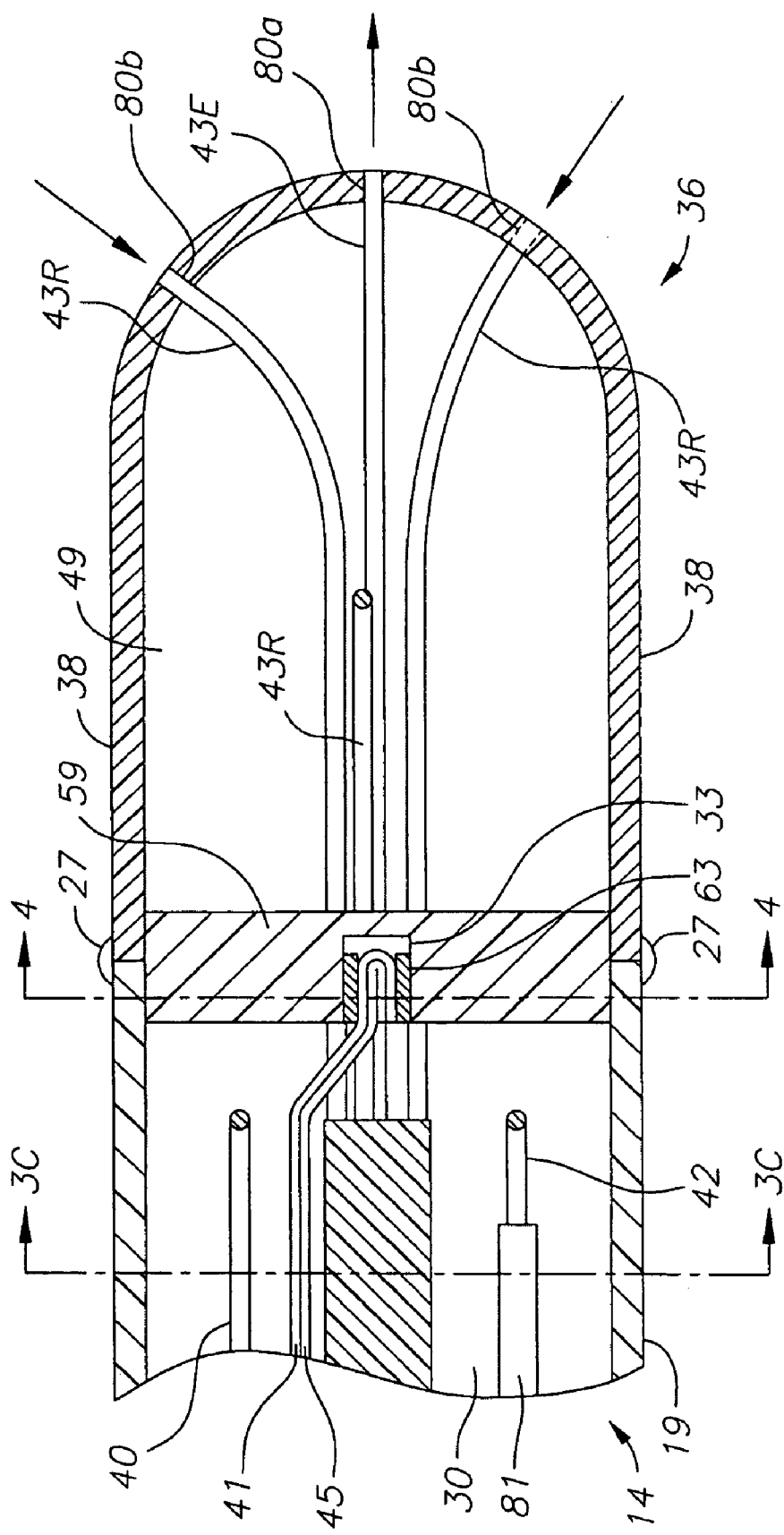
FIG. 3A is a side cross-sectional view of an embodiment of a tip electrode and a distal portion of an intermediate section, taken along a first diameter.
Figure 3B:
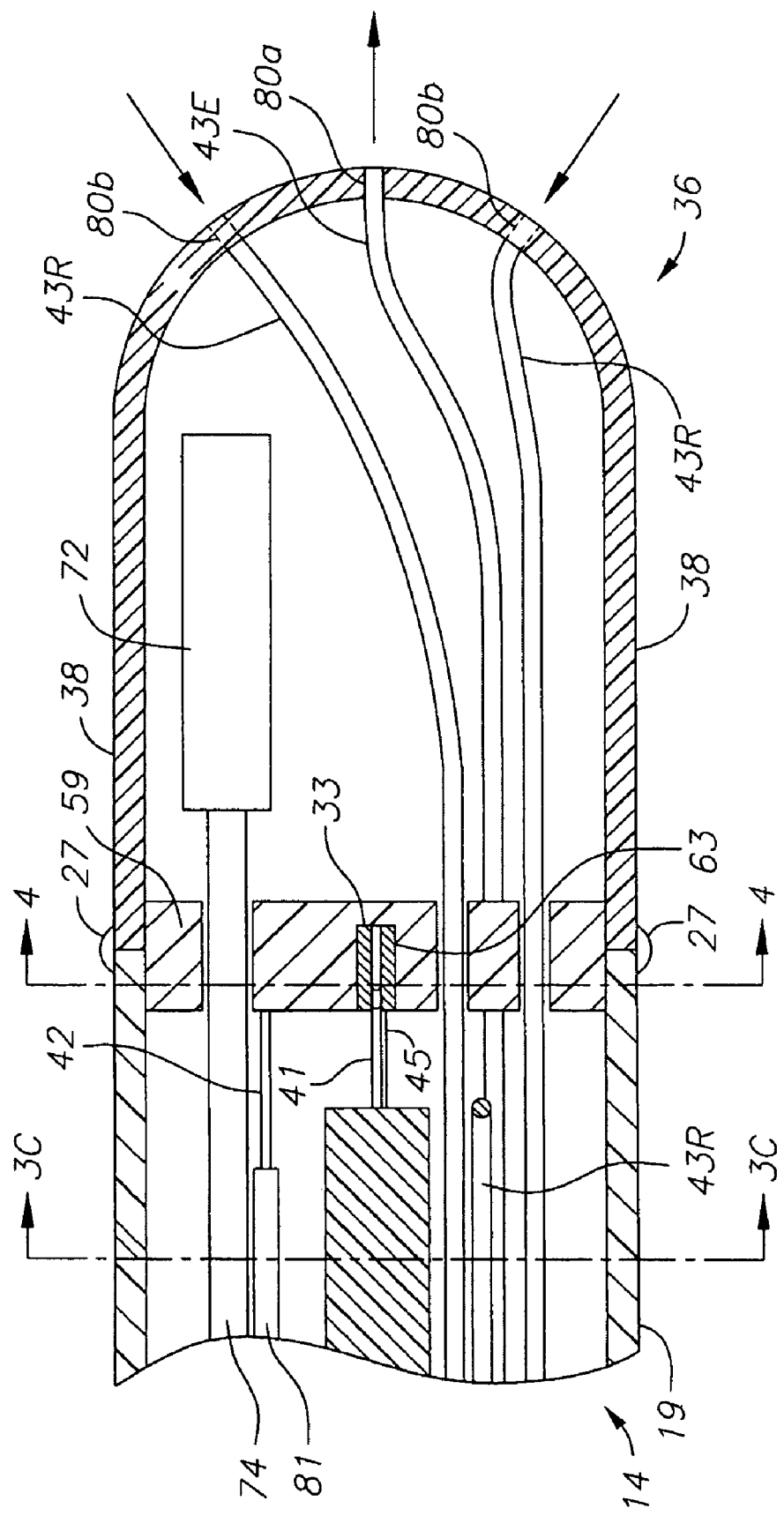
FIG. 3B is a side cross-sectional view of an embodiment of a tip electrode and a distal portion of an intermediate section, taken along a second diameter generally perpendicular to the first diameter of FIG. 3A.
Figure 3C:
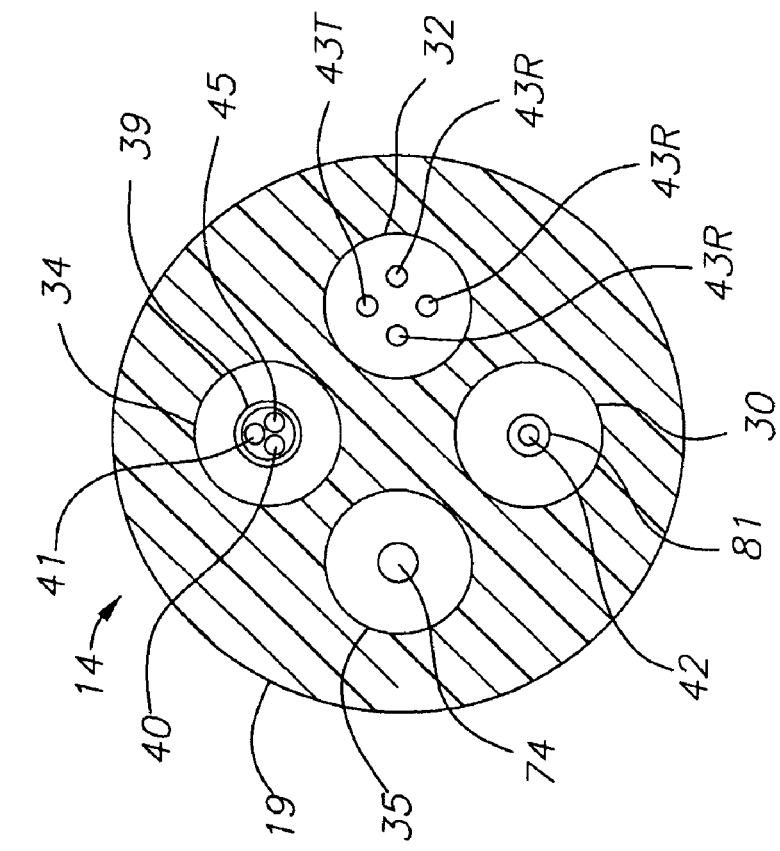
FIG. 3C is a longitudinal cross-sectional view of an embodiment of an intermediate section of FIGS. 3A and 3B, taken along line 3C-3C.

Referring also to FIGS. 3A, 3B and 3C, the intermediate section 14 comprises a shorter section of tubing 19 having multiple lumens. The tubing 19 is made of a suitable non-toxic material that is preferably more flexible than the catheter body 12. A suitable material for the tubing 19 is non-braided polyurethane. The outer diameter of the intermediate section 14, like that of the catheter body 12, is preferably no greater than about 8 french, more preferably 7 french. The size and number of the lumens is not critical. In an embodiment, the intermediate section 14 has an outer diameter of about 7 french (0.092 inch). The tubing has a first off-axis lumen 30, a second off-axis lumen 32, a third off-axis lumen 34 and a fourth off-axis lumen 35, that are generally about the same size, each having a diameter of from about 0.032 inch to about 0.038 inch, preferably 0.036 inch. In the illustrated embodiment, the puller wire 42 extends through the first lumen 30 and optical waveguides, e.g., the fiber optic cables 43, extend through the second lumen 32. The electrode lead wire 40 extends through the third lumen 34. The thermocouple wires 41 and 45 can also extend through the third lumen 34, and an electromagnetic sensor cable 74 can extend through the fourth lumen 35.

As best shown in FIGS. 2A and 2B, the catheter body 12 in one embodiment is attached to the intermediate section 14 by means of an outer circumferential notch 24 configured in the proximal end of the tubing 19 that receives the inner surface of the outer wall 22 of the catheter body 12. The intermediate section 14 and catheter body 12 are attached by glue or the like. Before the intermediate section 14 and catheter body 12 are attached, the stiffening tube 20 is inserted into the catheter body 12. The distal end of the stiffening tube 20 is fixedly attached near the distal end of the catheter body 12 by forming a glue joint 23 with polyurethane glue or the like. Preferably a small distance, e.g., about 3 mm, is provided between the distal end of the catheter body 12 and the distal end of the stiffening tube 20 to permit room for the catheter body 12 to receive the notch 24 of the intermediate section 14. If no compression coil is used, a force is applied to the proximal end of the stiffening tube 20, and, while the stiffening tube 20 is under compression, a first glue joint (not shown) is made between the stiffening tube 20 and the outer wall 22 by a fast drying glue, e.g., cyanoacrylate. Thereafter a second glue joint 26 is formed between the proximal ends of the stiffening tube 20 and outer wall 22 using a slower drying but stronger glue, e.g., polyurethane.

If desired, a spacer can be located within the catheter body between the distal end of the stiffening tube and the proximal end of the tip electrode. The spacer provides a transition in flexibility at the junction of the catheter body and intermediate section, which allows this junction to bend smoothly without folding or kinking. A catheter having such a spacer is described in U.S. patent application Ser. No. 08/924,616, entitled "Steerable Direct Myocardial Revascularization Catheter", the entire disclosure of which is incorporated herein by reference.

As illustrated in FIGS. 3A and 3B, the tip electrode 36 extends from the distal end of the intermediate section 14. In the illustrated embodiment, the tip electrode has a diameter about the same as the outer diameter of the tubing 19 of the intermediate section 14. The intermediate section 14 and the tip electrode are attached by glue 27 or the like applied circumferentially around a junction of the tubing 19 and the tip electrode 36. Moreover, the components extending between the intermediate section 14 and the tip electrode, e.g., the lead wire 40, the thermocouple wires 41 and 45, and the puller wire 42, help keep the tip electrode on the intermediate section.

In the illustrated embodiment, the tip electrode 36 has a generally hollow distal portion. The tip electrode comprises a shell 38 of generally uniform thickness and a press-fit alignment member or plug 59 positioned at or near the proximal end of the shell to seal the hollow distal portion. The shell and the plug are formed from any suitable material that is both thermally and electrically conductive which allows for radio frequency ablation using an RF generator. Such suitable materials include, without limitation, platinum, gold alloy, or palladium alloy. A tip electrode and method for manufacturing same are disclosed in application Ser. No. 11/058,434, filed Feb. 14, 2005, the entire disclosure of which is hereby incorporated by reference.

As discussed in detail further below, the alignment member 59 serves to stabilize, secure and/or support the various components extending into the tip electrode. The alignment member 59 has designated passages for the fiber optic components extending into the tip electrode and is situated at the proximal end of the shell 38 to define a chamber 49 in the distal end of the electrode 36 with a size and dimensions that accommodate the relatively limited flexure of the fiber optics while providing multi-directional radiation and/or collection of light at the tip electrode. The alignment member 59 allows the fiber optic cables 43 to be consistently in an optimal configuration inside the tip electrode to transmit and receive light energy from outside the tip electrode. The tip electrode 36 allows for sufficient space within to provide an optical termination and a stabilizing fixture for the fiber optic cables, and to house and carry components for enabling RF ablation and deflection with any curve shape. This construction design is intended to reduce machining costs and provide a deflection radii that facilitates the use of fiber optic cables in ablation catheters.

A tip electrode may have an effective length, i.e., from its distal end to the distal end of the intermediate section 14, between about 3.5 mm to about 7.5 mm, and an actual length, i.e., from its distal end to its proximal end, between about 4.0 mm to about 8.mm. The wall thickness may be generally equal to or greater than 0.004 inches.

The tip electrode 36 is energized for RF ablation by the lead wire 40 that extends through the third lumen 34 of intermediate section 14, the central lumen 18 of the catheter body 12, and the control handle 16, and terminates at its proximal end in an input jack (not shown) that may be plugged into an appropriate monitor (not shown). The portion of the lead wire 40 extending through the central lumen 18 of the catheter body 12, control handle 16 and distal end of the intermediate section 14 is enclosed within the protective sheath 39, which can be made of any suitable material, preferably Teflon RTM. The protective sheath 39 is anchored at its distal end to the distal end of the intermediate section 14 by gluing it in the lumen 34 with polyurethane glue or the like. The lead wire 40 is attached to the tip electrode 36 by any conventional technique. In the illustrated embodiment, connection of the lead wire 40 to the tip electrode 36 is accomplished, for example, by welding the distal end of the lead wire 40 into a first blind hole 31 (FIG. 3D) in the alignment member 59 of the tip electrode 36.

A temperature sensing means is provided for the tip electrode 36 in the disclosed embodiment. Any conventional temperature sensing means, e.g., a thermocouple or thermistor, may be used. With reference to FIGS. 3A and 3B, a suitable temperature sensing means for the tip electrode 36 comprises a thermocouple formed by a wire pair. One wire of the wire pair is the copper wire 41, e.g., a number 40 copper wire. The other wire of the wire pair is the constantan wire 45, which gives support and strength to the wire pair. The wires 41 and 45 of the wire pair are electrically isolated from each other except at their distal ends where they contact and are twisted together, covered with a short piece of plastic tubing 63, e.g., polyimide, and covered with epoxy. The plastic tubing 63 is then attached in a second blind hole 33 of the tip electrode 36 (FIG. 3B), by epoxy or the like. The wires 41 and 45 extend through the third lumen 34 in the intermediate section 14. Within the catheter body 12 the wires 41 and 45 extend through the central lumen 18 within the protective sheath 39 along with the lead wire 40. The wires 41 and 45 then extend out through the control handle 16 and to a connector (not shown) connectable to a temperature monitor (not shown). Alternatively, the temperature sensing means may be a thermistor. A suitable thermistor for use in the present invention is Model No. AB6N2-GC14KA143T/37C sold by Thermometrics (New Jersey).

Figure 3D:
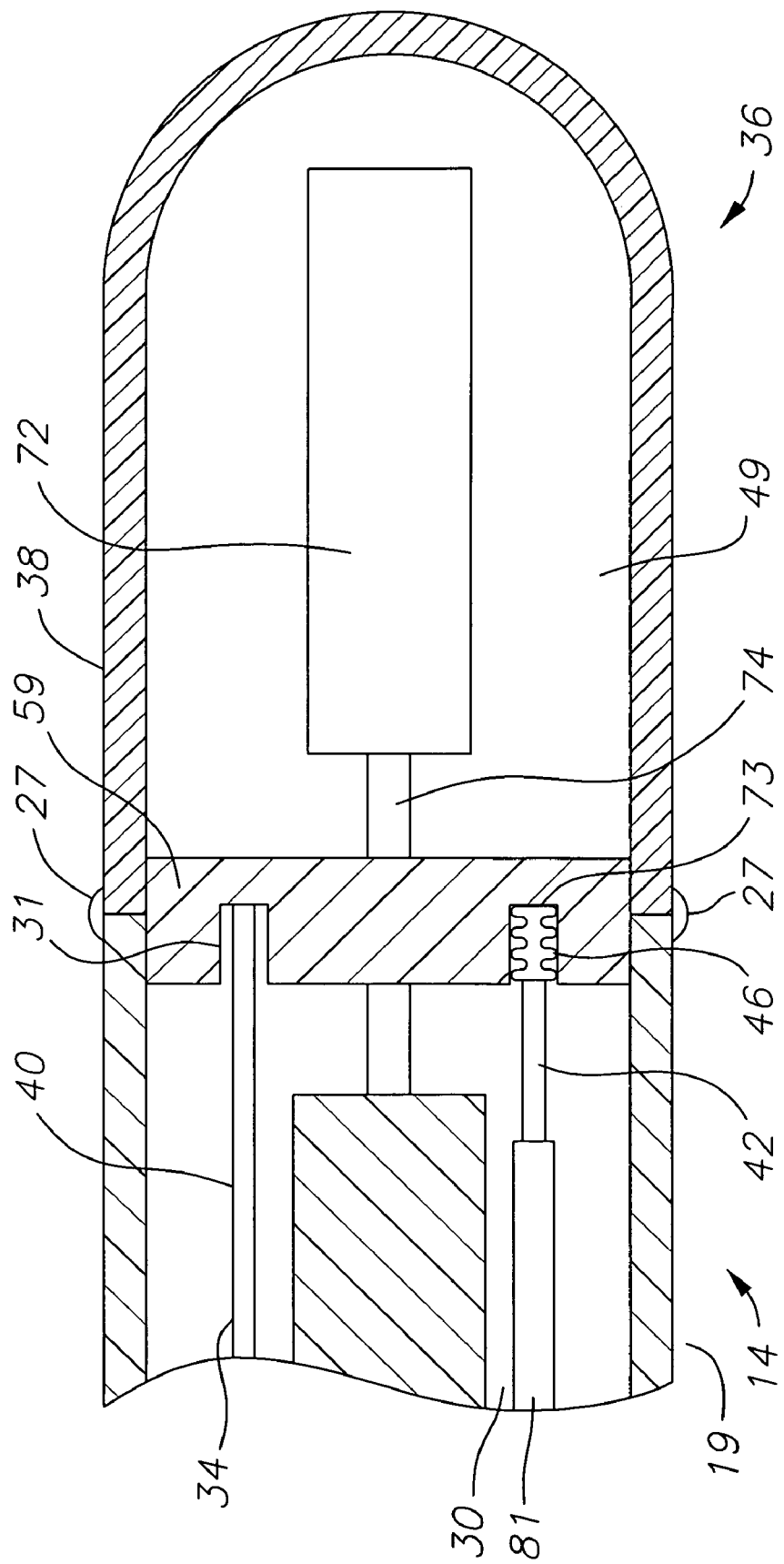
FIG. 3D is a side cross-sectional view of the embodiment of the tip electrode and distal portion of the intermediate section of FIG. 3B, taken along an axis generally parallel to but laterally offset from the first diameter of FIG. 3A, the axis intersecting distal ends of a puller wire and a lead wire as anchored in an alignment member of the tip electrode.

Referring to FIGS. 2A, 3A and 3D, the puller wire 42 as part of a means for deflecting the catheter extends through the catheter body 12, is anchored at its proximal end to the control handle 16, and is anchored at its distal end to the tip electrode 36. The puller wire is made of any suitable metal, such as stainless steel or Nitinol, and is preferably coated with Teflon.RTM. or the like. The coating imparts lubricity to the puller wire. The puller wire preferably has a diameter ranging from about 0.006 to about 0.010 inches.

The compression coil 44 is situated within the catheter body 12 in surrounding relation to the puller wire. The compression coil 44 extends from the proximal end of the catheter body 12 to the proximal end of the intermediate section 14 (FIG. 2). The compression coil is made of any suitable metal, preferably stainless steel, and is tightly wound on itself to provide flexibility, i.e., bending, but to resist compression. The inner diameter of the compression coil is preferably slightly larger than the diameter of the puller wire 42. The Teflon.RTM. coating on the puller wire allows it to slide freely within the compression coil. If desired, particularly if the lead wire 40 is not enclosed by a protective sheath 39, the outer surface of the compression coils can be covered by a flexible, non-conductive sheath, e.g., made of polyimide tubing, to prevent contact between the compression coils and any other wires within the catheter body 12.

As shown in FIG. 2A, the compression coil 44 is anchored at its proximal end to the proximal end of the stiffening tube 20 in the catheter body 12 by glue joint 50 and at its distal end to the intermediate section 14 by glue joint 51. Both glue joints 50 and 51 preferably comprise polyurethane glue or the like. The glue may be applied by means of a syringe or the like through a hole made between the outer surface of the catheter body 12 and the central lumen 18. Such a hole may be formed, for example, by a needle or the like that punctures the outer wall 22 of the catheter body 12 and the stiffening tube 20 which is heated sufficiently to form a permanent hole. The glue is then introduced through the hole to the outer surface of the compression coil 44 and wicks around the outer circumference to form a glue joint about the entire circumference of the compression coil.

With reference to FIGS. 2A, 3A and 3C, the puller wire 42 extends into the first lumen 30 of the intermediate section 14. The puller wire 42 is anchored at its distal end to the tip electrode 36 within the third blind hole 73 in the alignment member 59, as shown in FIG. 3D. A method for anchoring the puller wire 42 within the tip electrode 36 is by crimping metal tubing 46 to the distal end of the puller wire 42 and soldering the metal tubing 46 inside the blind hole 73. Anchoring the puller wire 42 within the alignment member 59 provides additional support, reducing the likelihood that the tip electrode 36 will fall off. Alternatively, the puller wire 42 can be attached to the side of the tubing 19 of the intermediate section 14 as understood by one of ordinary skill in the art. Within the first lumen 30 of the intermediate section 14, the puller wire 42 extends through a plastic, preferably Teflon-.RTM., sheath 81, which prevents the puller wire 42 from cutting into the wall of the intermediate section 14 when the intermediate section is deflected.

Longitudinal movement of the puller wire 42 relative to the catheter body 12, which results in deflection of the tip electrode 36, is accomplished by suitable manipulation of the control handle 16. A suitable control handle is described in U.S. Pat. No. 6,602,242, the entire disclosure of which is hereby incorporated by reference.

In the illustrated embodiment of FIGS. 3A, 3B and 3D, the tip electrode 36 carries an electromagnetic sensor 72. The electromagnetic sensor 72 is connected to the electromagnetic sensor cable 74, which extends through a passage 75 (FIG. 4) in the alignment member 39, the third lumen 35 of the tip electrode 36, through the central lumen 18 of the catheter body 12, and into the control handle 16. As shown in FIG. 1, the electromagnetic sensor cable 74 then extends out the proximal end of the control handle 16 within an umbilical cord 78 to a sensor control module 75 that houses a circuit board (not shown). Alternatively, the circuit board can be housed within the control handle 16, for example, as described in U.S. patent application Ser. No. 08/924,616, entitled "Steerable Direct Myocardial Revascularization Catheter", the entire disclosure of which is incorporated herein by reference. The electromagnetic sensor cable 74 comprises multiple wires encased within a plastic covered sheath. In the sensor control module 75, the wires of the electromagnetic sensor cable 74 are connected to the circuit board. The circuit board amplifies the signal received from the electromagnetic sensor 72 and transmits it to a computer in a form understandable by the computer by means of the sensor connector 77 at the proximal end of the sensor control module 75, as shown in FIG. 1. Because the catheter can be designed for single use only, the circuit board may contain an EPROM chip which shuts down the circuit board approximately 24 hours after the catheter has been used. This prevents the catheter, or at least the electromagnetic sensor, from being used twice. Suitable electromagnetic sensors for use with the present invention are described, for example, in U.S. Pat. Nos. 5,558,091, 5,443,489, 5,480,422, 5,546,951, 5,568, 809, and 5,391,199 and International Publication No. WO 95/02995, the disclosures of which are incorporated herein by reference. An electromagnetic mapping sensor 72 may have a length of from about 6 mm to about 7 mm and a diameter of about 1.3 mm.

In accordance with a feature of the present invention, the catheter 10 is adapted to facilitate optically-based real-time assessment of ablation tissue characteristics, including without limitation, lesion formation, depth of penetration of the lesion, cross-sectional area of the lesion, formation of char during ablation, recognition of char during ablation, differentiation of char from non-charred tissue, formation of coagulum around the ablation site, differentiation of coagulated from non-coagulated blood, differentiation of ablated from healthy tissue, tissue proximity, and recognition of steam formation in the tissue for prevention of steam pop. These assessments are accomplished by measuring the light intensity at one or more wavelengths that is recaptured at the catheter tip resulting from the light radiated from the catheter tip onto ablated tissue.

As shown in FIGS. 2A, 3A and 3B, optical waveguides, e.g., the fiber optic cables 43 are provided in the catheter to illuminate a lesion for purposes of collecting optical data to conduct the aforementioned assessments. The fiber optic cables 43 transmit light to the tip electrode 36 and collect light at the tip electrode. The fiber optic cables 43 are protectively housed in the catheter along its length. They extend through the lumen 18 of the catheter body 12, through the second lumen 32 of the intermediate section 14 and into the tip electrode 36.

Figure 4:
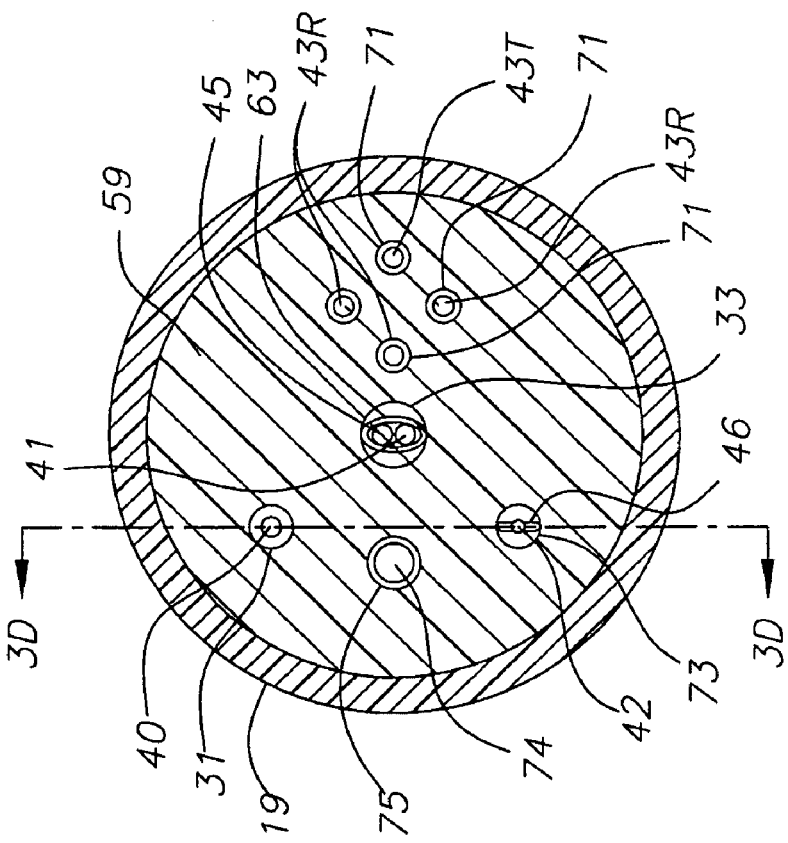
FIG. 4 is a longitudinal cross-section of an embodiment of a tip electrode of FIGS. 3A and 3B, taken along line 4-4.

It is understood by one of ordinary skill in the art that optical waveguides and fiber optic cables in general serve to transmit optical energy from one end to the other, although these are not exclusive. Accordingly, one or more of the cables 43 may function as a light emitting cable by transmitting light energy to the tip electrode 36 from an external and/or internal light source, and one or more of the other cables 43 may function as a light receiving cable in the tip electrode 36 by collecting light energy at the tip electrode and transmitting it to an optical processing system. In either function as a light transmitting or light receiving cable, each of the fiber optic cables 43 passes through a passage 71 configured in the alignment member 59, as shown in FIG. 4, and extends distally toward a respective opening 80 configured in the distal region of the shell 38 of the tip electrode 36, as shown in FIGS. 3A and 3B. The distal ends of the fiber optic cables 43 are received and fixedly secured in the openings by glue, adhesive or the like. Accordingly, light can be emitted from and be collected at the tip electrode by the fiber optic cables 43.

In accordance with a feature of the present invention, the shell 38 and the alignment member 59 of the tip electrode 36 are configured to provide the chamber 49 with sufficient length and width to accommodate the flexure of the fiber optic cables as they extend between the alignment member 59 and the openings 80. To that end, the openings 80 and the passages 71 in the alignment member 29 are positioned relative to each other such that the flexure of the fiber optic cables therebetween does not exceed about 30 degrees within the space constraints of the tip dimensions mentioned above.

With reference to FIG. 3, the openings 80 are provided in the distal portion of the shell 38. There is a center opening 80a which is located generally at the most distal location on the shell along the longitudinal axis of the electrode 36 for on-axis transmission or collection at the tip electrode. There are also off-center openings 80b which are located proximal of the opening 80a for off-axis transmission or collection with a greater radial component. It is understood by one of ordinary skill in the art that the number and arrangement of the openings 80a and 80b may be varied as appropriate or desired. For example, the number of off-center openings 80b may range between about 3 to 6, arranged at angles between about 120 to 60 degrees, respectively, about the center opening 80a. For example, there can be three openings 80b equally offset from each other at about 120 degrees, four openings 80b equally offset from each other at about 90 degrees, five openings 80b equally offset from each other at about 72 degrees, or six openings 80b equally offset from each other at about 60 degrees.

In the illustrated embodiment of FIGS. 3, 3A and 3B, there is one opening 80a for a single fiber optic cable 43E delivering light energy from the opening 80a and there are three openings 80b for three fiber optic cables 43R receiving light energy through the openings 80b. The three openings 80b are generally equi-spaced from each other and from the opening 80a, and equi-angular about the opening 80a.

The shell 38 is configured with a generally spherical, parabolic or at least rounded convex distal portion such that the tip electrode 36 remains of an atraumatic design and provides an on-axis section 100a for the center opening 80a that opens along the longitudinal axis of the tip electrode, and an off-axis section 100b for the off-center openings 80b that open in an off-axis direction.

Figure 5:
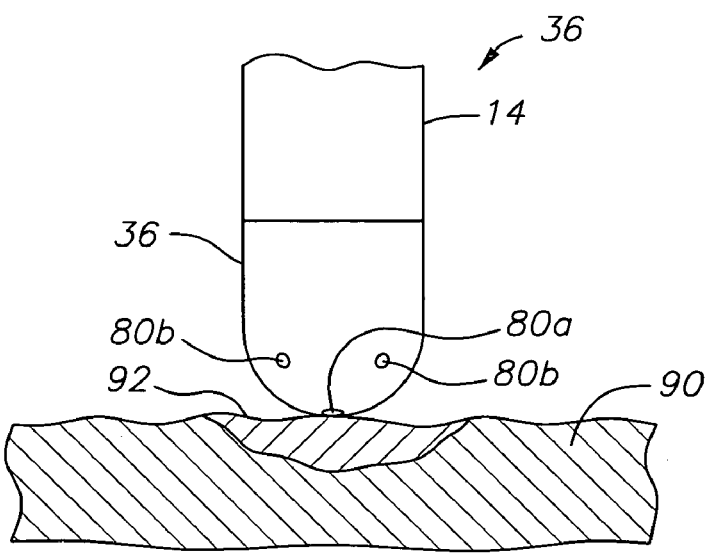
FIG. 5 is a side view of an embodiment of a tip electrode whose longitudinal axis is generally perpendicular to tissue surface.

With reference to FIG. 5, as lesion 92 forms in the tissue 90 from RF ablation carried out by tip electrode 36 (or by another catheter), characteristics of the tissue are altered as understood by one of ordinary skill in the art. As the tip electrode illuminates the lesion with light from the fiber optic cable 43E through the opening 80a, the light is scattered and/or reflected back toward the tip electrode 36. Such light having interacted or otherwise having been affected by the lesion bears qualitative and quantitative information about the lesion 92 as it is collected by the fiber optic cables 43R through the openings 80b. It is understood by one of ordinary skill in the art that the number of transmitting and receiving fiber optic cables, the corresponding openings and the pattern of the openings on the shell may be varied as appropriate or desired. It is further understood that the fiber optic cables 43E and 43R may be any suitable optical wave guide wherein light introduced at one of the cable is guided to the other end of the cable with minimal loss. Each of the cables 43E and 43R may be a single fiber optic cable or fiber bundles. They may be single mode (also known as mono-mode or uni-mode), multi-mode (with step index or graded index) or plastic optical fiber (POF), depending on a variety of factors, including but not limited to transmission rate, bandwidth of transmission, spectral width of transmission, distance of transmission, diameter of cable, cost, optical signal distortion tolerance and signal attenuation, etc.

In accordance with a feature of the present invention, the portion of each fiber optic cables 43 within the passages 71 is fixedly secured to the alignment member 59 by glue, adhesive or the like to prevent distal, proximal or rotational movement of the portion of the fiber optic cables in and distal the alignment member 59. As its name suggests, the alignment member 59 maintains alignment of each fiber optic cable within the tip electrode. In that regard, the passages 71 are generally aligned with the second lumen 32 of the intermediate section 14 to minimize stress and strain that can cause breakage of the fiber optic cables in the transition between the intermediate section 14 and the tip electrode 36. The portion of the cables 43 proximal the alignment member 59 remains generally parallel with the catheter body 12 and intermediate section 14, and moves and bends with them. As shown in FIGS. 2B, 3A and 4A, the cables 43 are protectively housed within the catheter from the tip electrode 36 to the control handle 16.

Figure 6:
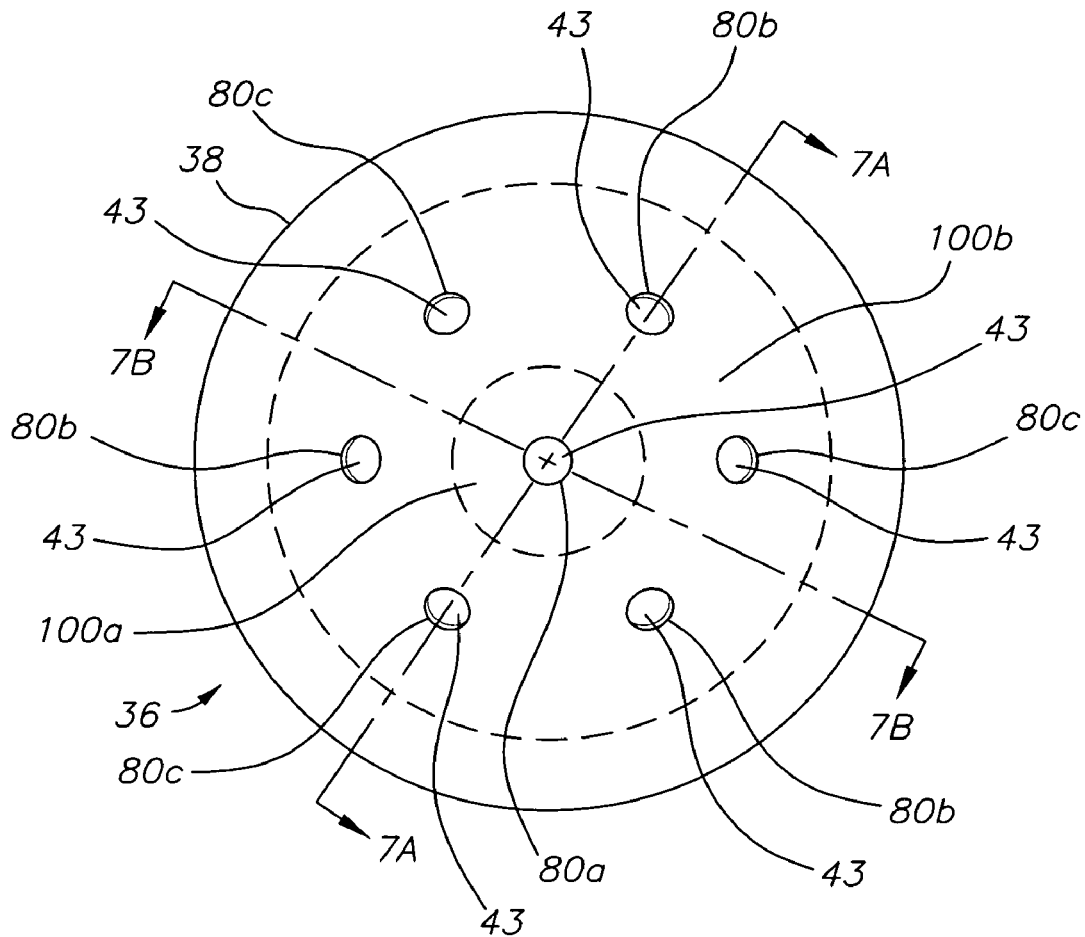
FIG. 6 is an end view of the distal end of an alternative embodiment of a tip electrode showing a center opening, a plurality of off-center openings and additional irrigation openings.
Figure 7A:
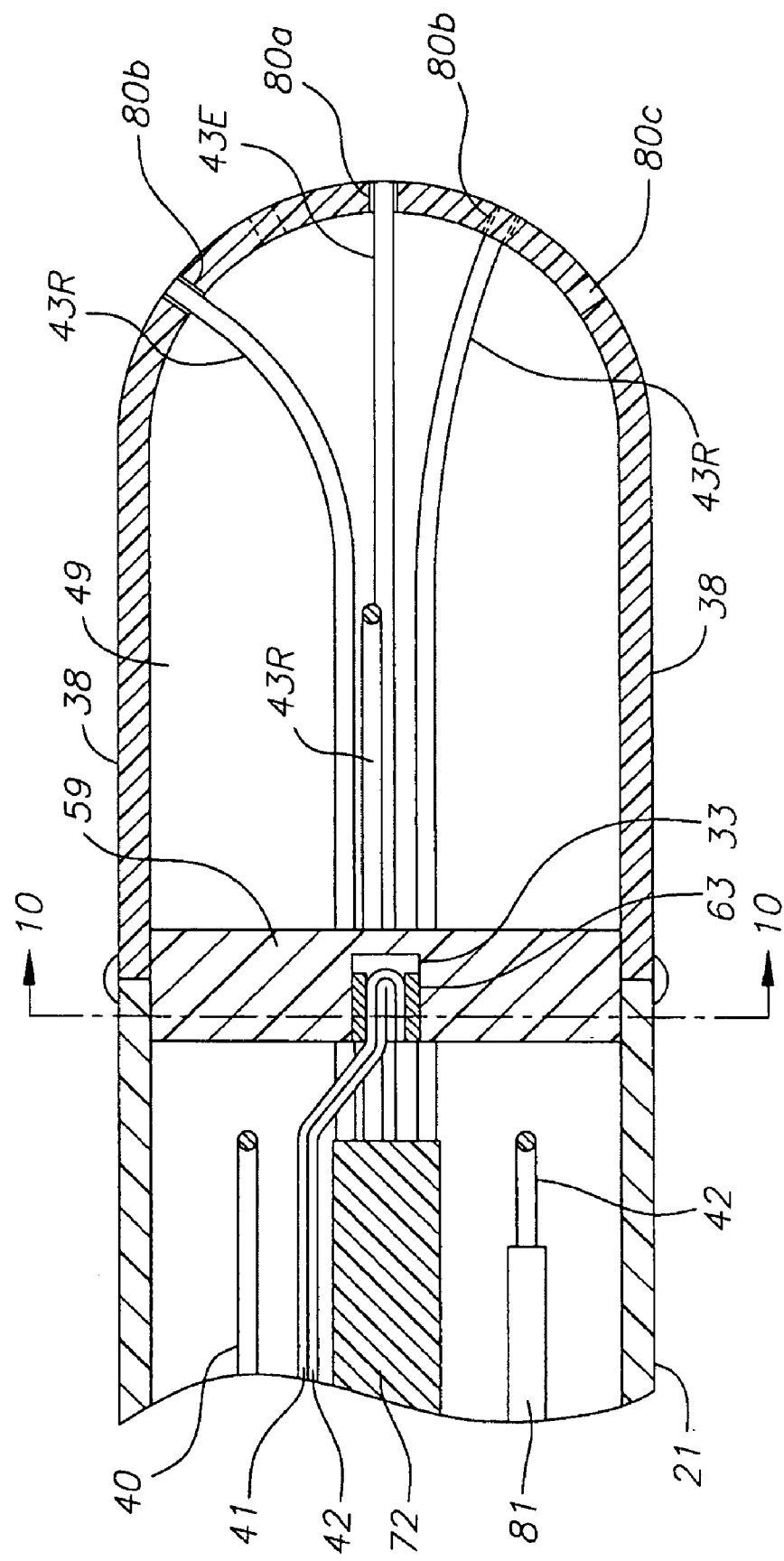
FIG. 7A is a side cross-sectional view of another embodiment of a tip electrode and a distal portion of an intermediate section, taken along a first diameter.
Figures 9, 10:
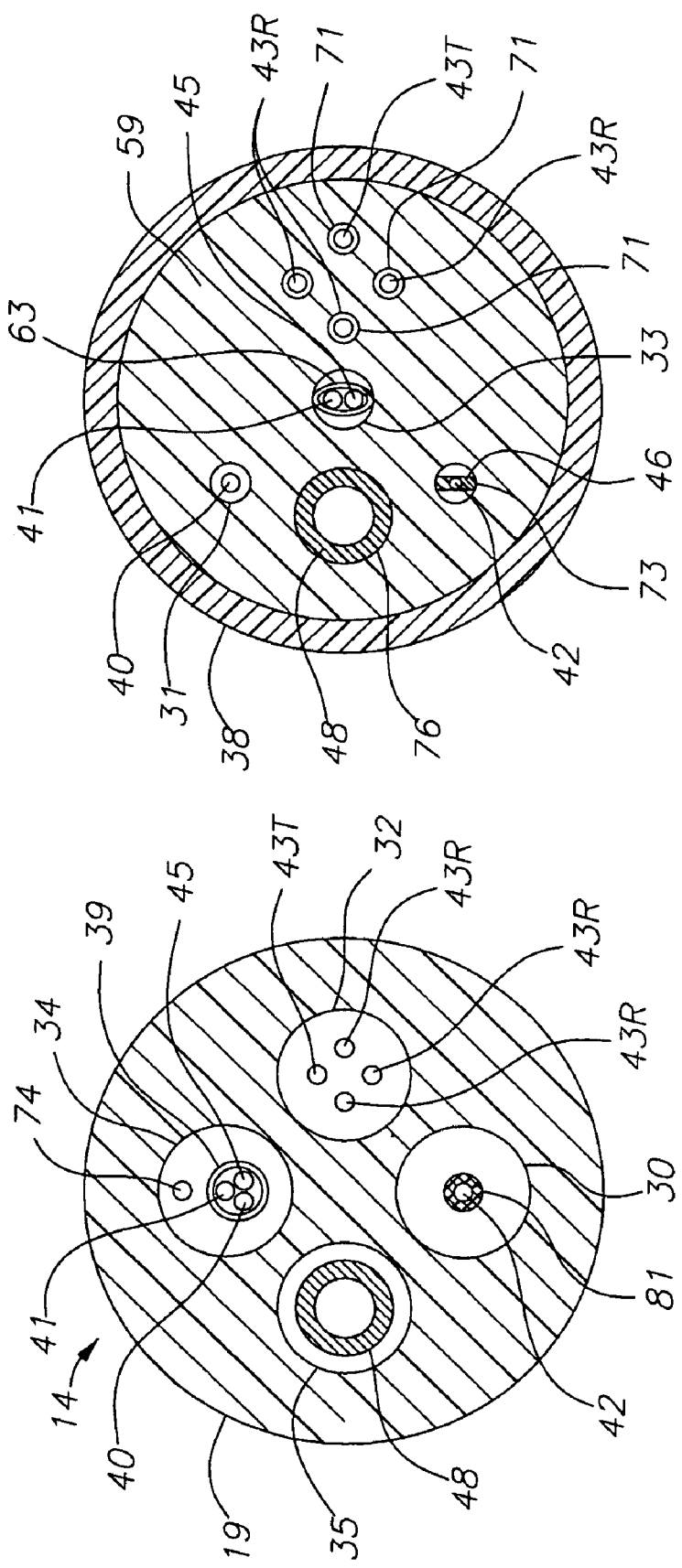
FIG. 9 is a longitudinal cross-sectional view of the intermediate section of FIG. 8, taken along line 9-9.
FIG. 10 is a longitudinal cross-sectional view of the tip electrode of FIGS. 7A and 7B, taken along line 10-10.

The openings 80 are sized to receive the distal ends of the cables 43 in a generally snug-fit fashion. However, in an alternative embodiment as illustrated in FIGS. 7A and 7B, the openings 80 are sized larger than the distal ends of the cables 43 to allow fluid (e.g. saline) to flow through the openings around the cable distal ends to reach outside the tip electrode for cooling the tip electrode and ablation site and/or enabling larger and deeper lesions. Additional openings 80c, as shown in FIG. 6, that are not occupied by a fiber optic cable may be provided allowing further irrigation of the tip electrode. The fluid is fed into the chamber 49 by an irrigation means, as shown in FIG. 7B, that include a tube segment 48 extending from the distal end of the fourth lumen 35 of the intermediate section 14 and a passage 76 in the plug 59 (FIG. 10). The distal end of the segment 48 is anchored in the passage 76 and the proximal end is anchored in the fourth lumen 35 by polyurethane glue or the like. Accordingly, the passage 76 is generally aligned with the fourth lumen 35 of the intermediate section 14. The segment 48, like the puller wires 42, provides additional support for the tip electrode. The irrigation tube segment 48 is in communication with a proximal infusion tube segment (not shown) that extends through the central lumen 18 of the catheter body 12 and terminates in the proximal end of the fourth lumen 35 of the intermediate section 14. The proximal end of the first infusion tube segment extends through the control handle 16 and terminates in a luer hub 90 (FIG. 11) or the like at a location proximal to the control handle. In practice, fluid may be injected by a pump (not shown) into the infusion tube segment through the luer hub 90, through the infusion tube segment 48, into the chamber 49 in the tip electrode 36, and out the openings 80. The infusion tube segments may be made of any suitable material, and is preferably made of polyimide tubing. A suitable infusion tube segment has an outer diameter of from about 0.32 inch to about 0.036 inch and an inner diameter of from about 0.28 inch to about 0.032 inch.

The pump maintains the fluid at a positive pressure differential relative to outside the chamber 49 so as to provide a constant unimpeded flow or seepage of fluid outwardly from the chamber 49 which continuously seeps out from the openings 80.

Figure 8:
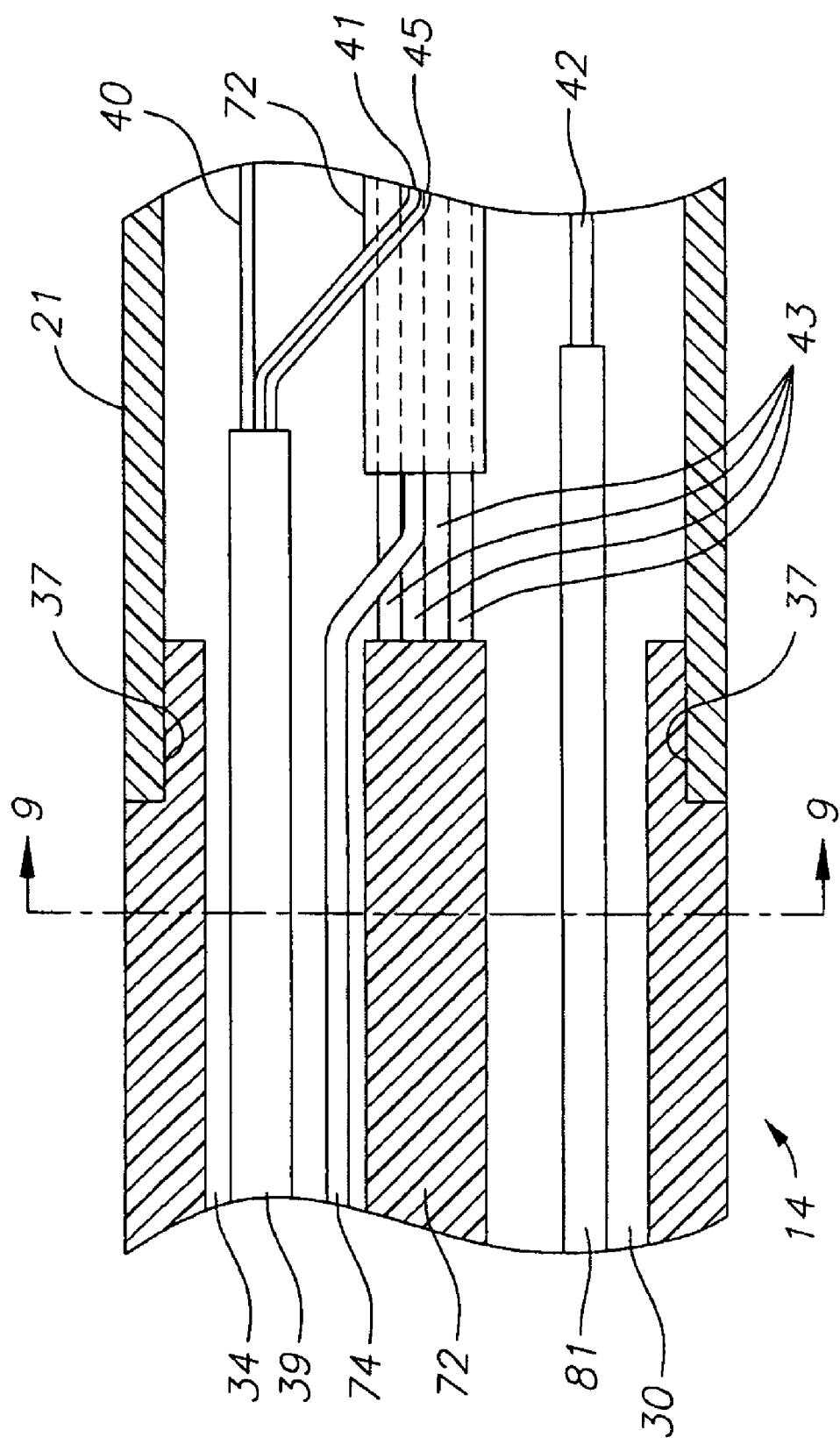
FIG. 8 is a side cross sectional view of an alternative embodiment of an intermediate section, including a junction with a housing member.

In the illustrated embodiment of FIGS. 7A, 7B and 8, a housing 21 extends between the intermediate section 14 and the tip electrode 36 so that the electromagnetic sensor 72 can remain near the tip electrode and remain dry. The housing 21 (e.g., a plastic tube member) is attached to the tubing 19 of the intermediate section by creating a circumferential notch 37 in the distal end of the tubing 19, placing the proximal end of the housing 21 on the distal end of the tubing 19, and filling the notch 37 with glue. The distal end of the housing 21 and the tip electrode 36 are attached by glue at a seam 69. All the components extending into or through the alignment member 59 help keep the tip electrode 36 attached to the housing 21.

It is understood by one of ordinary skill in the art that any desired aspects of the different embodiments described herein may be incorporated within a catheter tip section so as to suit the needs and desires in a particular use and application. For example, the embodiment of FIGS. 7A, 7B and 8 need not include irrigation, but the em sensor 72 can nevertheless be housed outside of the chamber 49, in tubing 21, especially if there is insufficient space in the chamber 49 to contain both the em sensor 72 and the fiber optic cables 43.

Figure 11:
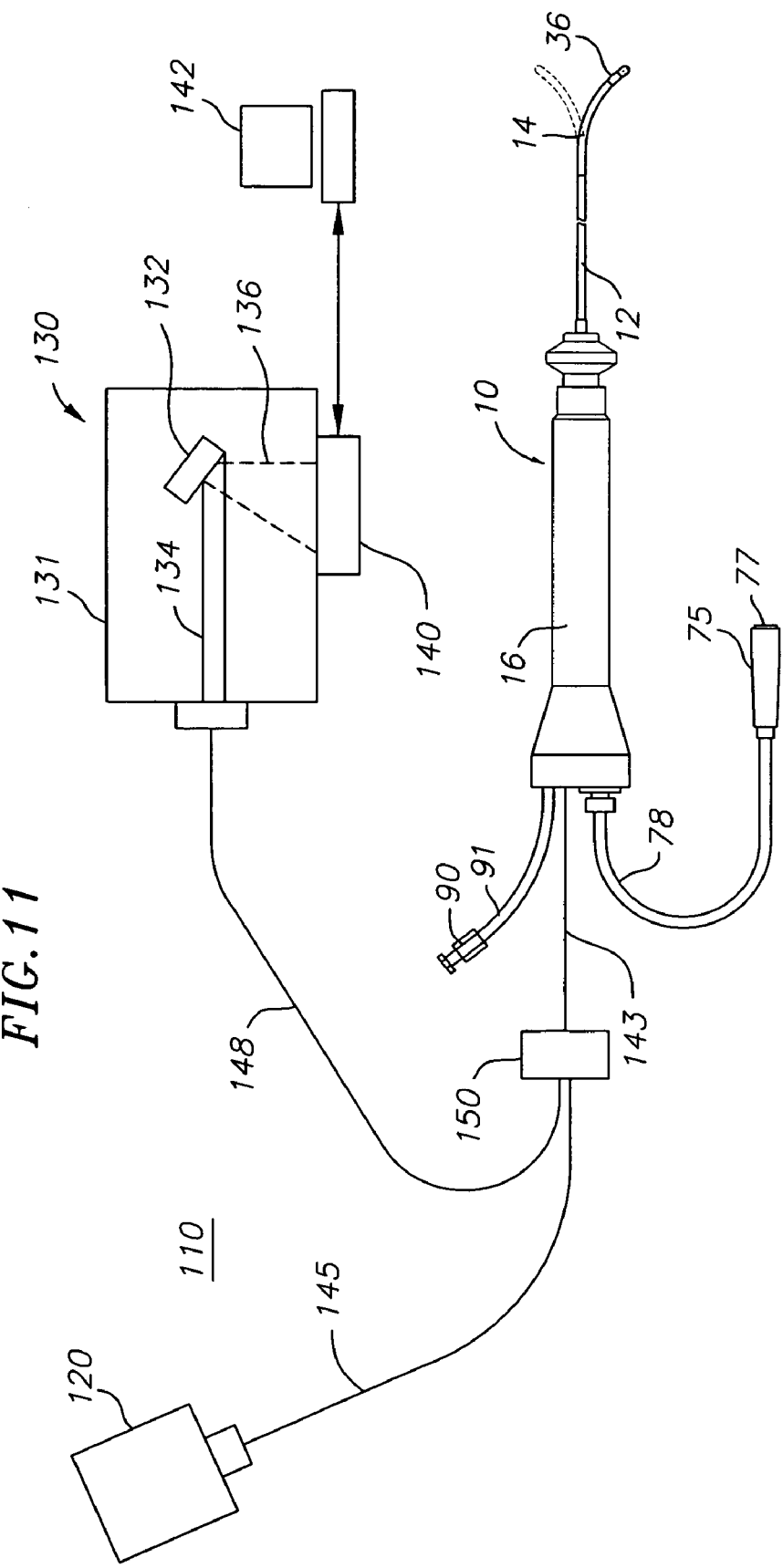
FIG. 11 is a schematic drawing showing components of an embodiment of an optical processing system for use with the catheter of the present invention.

With reference to FIG. 11, an optical processing system 110 for optically evaluating ablation tissue using the catheter 10 is illustrated. A light source 120 supplies a broadband (white; multiple wavelengths) light and/or laser light (single wavelength) radiation to the tip electrode 36 of the catheter 10 via couplings or connections 145 and 143 (couplings and connections used interchangeably herein), and light bearing lesion qualitative and quantitative information from the tip electrode is transmitted to a detection component 130 via connections 143 and 148. The detection component may comprise, for example, a wavelength selective element 131 that disperses the collected light into constituent wavelengths, and a quantification apparatus 140. The at least one wavelength selective element 131 includes optics 132, as are known in the art, for example, a system of lenses, mirrors and/or prisms, for receiving incident light 134 and splitting it into desired components 136 that are transmitted into the quantification apparatus 140.

The quantification apparatus 140 translates measured light intensities into an electrical signal that can be processed with a computer 142 and displayed graphically to an operator of the catheter 10. The quantification apparatus 140 may comprise a charged coupled device (CCD) for simultaneous detection and quantification of these light intensities. Alternatively, a number of different light sensors, including photodiodes, photomultipliers or complementary metal oxide semiconductor (CMOS) detectors may be used in place of the CCD converter. Information is transmitted from the quantification device 140 to the computer 142 where a graphical display or other information is generated regarding parameters of the lesion. A suitable system for use with the catheter 10 is described in U.S. application Ser. Nos. 11/281,179 and 11/281,853, the entire disclosures of which are hereby incorporated by reference.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter, comprising:
   a catheter body;
   a tip electrode distal the catheter body adapted for ablating tissue, the tip electrode having a shell, an alignment member, and a hollow distal portion, the alignment member positioned proximal the hollow space, the shell having openings.
   a plurality of optical waveguides adapted to transmit optical energy to and from the tip electrode, a distal portion of each waveguide extending through the hollow distal portion and terminating in the openings;
   wherein the alignment member fixedly secures the distal portion of each waveguide against movement relative to the alignment member and the shell.

2. A catheter of claim 1, further comprising irrigation means.

3. A catheter of claim 1, wherein the distal portion of each waveguide has a fixed flexure configuration within the hollow distal portion of the tip electrode.

4. A catheter of claim 1, wherein the openings include a center opening aligned with a longitudinal axis of the tip electrode and at least one off-center opening.

5. A catheter of claim 1, wherein the distal portion of each waveguide is directed to transmit or receive light energy at a different angle.

6. A catheter of claim 4, wherein there are three off-center openings configured equally offset from each other at about 120 degrees.

7. A catheter of claim 4, wherein there are four off-center openings configured equally offset from each other at about 90 degrees.

8. A catheter of claim 4, wherein there are five off-center openings configured equally offset from each other at about 72 degrees.

9. A catheter of claim 4, wherein there are six off-center openings configured equally offset from each other at about 60 degrees.

10. A catheter of claim 1, wherein the tip electrode is adapted for RF ablation.

11. A catheter of claim 1, wherein light energy received by a waveguide conveys a tissue parameter of a lesion illuminated by light energy transmitted by another waveguide.

12. A catheter of claim 11, wherein the tissue parameter includes at least one of the following: lesion formation, depth of penetration of lesion, cross-sectional area of lesion, formation of char during ablation, recognition of char during ablation, differentiation of char from non-charred tissue, formation of coagulum around the ablation site, differentiation of coagulated from non-coagulated blood, differentiation of ablated from healthy tissue, tissue proximity, evaluation of tissue health, status, and disease state, and recognition of steam formation in the tissue for prevention of steam pop.

13. A catheter of claim 1, wherein the tip electrode is made of thermally and electrically conductive material.

14. A catheter of claim 1, further comprising an electromagnetic location sensor carried at or near the tip electrode for producing electrical signals indicative of a location of the electromagnetic location sensor.

15. A catheter of claim 1, further comprising a temperature sensor.

16. A catheter according to claim 1, further comprising means for deflecting a section of the catheter body.

17. A catheter of claim 3, wherein the flexure configuration has a degree of flexure not greater than about 30 degrees.

* * * * *

UNITED STATES PATENT AND TRADEMARK OFFICE
CERTIFICATE OF CORRECTION

PATENT NO.       : 7,662,152 B2
APPLICATION NO.  : 11/453188
DATED            : February 16, 2010
INVENTOR(S)      : Sharareh et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 706 days.

Signed and Sealed this

Twenty-eighth Day of December, 2010

David J. Kappos
*Director of the United States Patent and Trademark Office*